United States Patent
Bonrath et al.

(10) Patent No.: US 9,309,194 B2
(45) Date of Patent: *Apr. 12, 2016

(54) INTERMEDIATES FOR THE VITAMIN A AND β-CAROTENE SYNTHESIS

(75) Inventors: Werner Bonrath, Basel (CH); Thomas Netscher, Basel (CH); Jan Schütz, Basel (CH); Bettina Wüstenberg, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/128,802

(22) PCT Filed: Jun. 14, 2012

(86) PCT No.: PCT/EP2012/061294
§ 371 (c)(1),
(2), (4) Date: Aug. 8, 2014

(87) PCT Pub. No.: WO2012/175398
PCT Pub. Date: Dec. 27, 2012

(65) Prior Publication Data
US 2015/0112091 A1    Apr. 23, 2015

(30) Foreign Application Priority Data
Jun. 22, 2011 (EP) .................... 11171071

(51) Int. Cl.
C07C 403/12 (2006.01)
C07C 403/16 (2006.01)
C07C 403/08 (2006.01)
C07C 403/24 (2006.01)
C07F 15/00 (2006.01)

(52) U.S. Cl.
CPC ............. *C07C 403/12* (2013.01); *C07C 403/08* (2013.01); *C07C 403/16* (2013.01); *C07C 403/24* (2013.01); *C07F 15/006* (2013.01); *C07C 2101/16* (2013.01)

(58) Field of Classification Search
CPC .. C07C 403/12; C07C 403/08; C07C 403/24; C07C 403/16; C07C 2101/16; C07F 15/006
See application file for complete search history.

(56) References Cited

U.S. PATENT DOCUMENTS 2,369,162 A   2/1945   Milas
4,064,162 A   12/1977  Oroshnik
9,040,742 B2* 5/2015   Bonrath et al. ............... 560/220

FOREIGN PATENT DOCUMENTS

GB    1034189 A  *  6/1966

OTHER PUBLICATIONS

International Search Report for PCT/EP2012/061294, mailed Sep. 20, 2012.
Bartik, T. et al., Bestimmung Der Raumerfuellung Von Tertiaeren Phosphanen Ueber 31p-Nmr-Spektroskopische Daten Von Trans-L2-Pdcl2-Komplexen, Journal of Organomettalic Chemistry, vol. 293, No. 3, (Oct. 1, 1985), pp. 343-351.
Reid, W. et al., "Neue, Potentiell Bakteriostatisch and Fungistatisch Wirksame Stoffe Auf De Basis Des 5-Methoxypent-4-en-2-in-1-ons Bzw.-1-imins", Archiv Der Pharmazie, vol. 316, No. 5, (Jan. 1, 1983), pp. 454-460.
Evans, D. et al., "Total Synthesis of (+)-Azaspiracid-1. An Exhibition of the Intricacies of Complex Molecule Synthesis", Journal of the Americal Chemical Society, vol. 130, No. 48, (Dec. 3, 2008), pp. 16295-16309.

* cited by examiner

*Primary Examiner* — Sudhakar Katakam
(74) *Attorney, Agent, or Firm* — Nixon & Vanderhye P.C.

(57) ABSTRACT

The present invention relates to compounds of formula (I) wherein $R^1$ signifies a $C_1$-$C_{15}$ alkyl moiety or a $C_2$ to $C_{18}$ alkenyl moiety, to their process of production as well as to their use in organic synthesis, especially as intermediates (building blocks) in the synthesis of vitamin A or β-carotene or derivatives thereof, or other carotenoids, e.g. canthaxanthin, astaxanthin or zeaxanthin, preferably vitamin A.

(1)

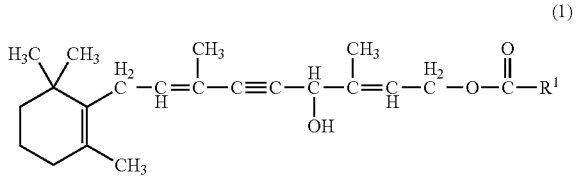

7 Claims, No Drawings

INTERMEDIATES FOR THE VITAMIN A AND β-CAROTENE SYNTHESIS

This application is the U.S. national phase of International Application No. PCT/EP2012/061294, filed 14 Jun. 2012, which designated the U.S. and claims priority to EP Application No. 11171071.1, filed 22 Jun. 2011, the entire contents of each of which are hereby incorporated by reference.

The present invention relates to new compounds, to their synthesis as well as to their use in organic synthesis, especially in the synthesis of vitamin A or β-carotene and derivatives thereof, e.g. canthaxanthin, astaxanthin or zeaxanthin. Especially to be mentioned is that the new compounds are useful as intermediates (building blocks) in the synthesis of vitamin A or β-carotene, preferably vitamin A.

Vitamin A (all-E)-retinol (vitamin A)

is an important ingredient for many applications. Vitamin A plays a role in a variety of functions throughout the body, such as e.g. vision process, gene transcription, immune function, bone metabolism, haematopoiesis, skin and cellular health and antioxidant function.

Due to the importance of vitamin A (and its derivatives) and the complexity of the synthesis thereof, there is always a need for improved processes of production.

The goal of the present invention was to find easily accessible compounds, which can then be used in an improved synthesis of vitamin A or β-carotene, preferably vitamin A. The aim was achieved by the compounds and the synthesis as disclosed and described below.

Compounds of formula (I) are not known from prior art. The invention relates to compounds of formula (I)

(I)

wherein $R^1$ signifies a $C_1$-$C_{15}$ alkyl moiety or a $C_2$-$C_{18}$ alkenyl moiety.

When R is a $C_1$-$C_{15}$ alkyl moiety, then preferably the alkyl moiety is linear. Especially preferred alkyl moieties are methyl, ethyl and pentadecyl.

When $R^1$ is a $C_2$-$C_{18}$ alkenyl moiety, compound of formula (I) can have more than three C—C double bonds. Preferably the alkenyl moiety is unbranched.

Compounds of formula (I) can be in any stereoisomeric form. The compounds of formula (I) can be in an all-E-form or in an all-Z-form, as well as in any other E/Z-form.

It is possible that the compound of formula (I) is in an isomerically pure form, but it is also possible that compound of formula (I) is a mixture of at least two isomeric forms.

These most preferred compounds of formula (I) are listed below as compounds of formula (Ia), (Ib) and (Ic):

(Ia)

(Ib)

(Ic)

Furthermore the present invention relates to processes for production of compounds of formula (I).

One suitable process for the production of compounds of formula (I) relates to a process wherein compounds of formula (II)

(II)

wherein $R^1$ has the same meanings as in formula (I), are reduced to compounds of formula (I).

Surprisingly we found that the reduction can be carried out using 2-methyl-CBS-oxazaborolidine/borane dimethyl sulfide (2-methyl-CBS-oxazaborolidine=1-methyl-3,3-diphenylhexahydropyrrolo[1,2-c][1,3,2]oxazaborole). The (S) or the (R) form as well as the racemate of 2-methyl-CBS-oxazaborolidine can be used. 2-Methyl-CBS-oxazaborolidines are usually applied in combination with borane dimethyl sulfide. 2-Methyl-CBS-oxazaborolidine and borane dimethyl sulfide are used in equimolar amounts (or in excess) in regard to the compounds of formula (II).

Usually the reaction is carried out in an organic solvent. Suitable solvents are ethers, e.g. THF, toluene, methyl-THF, methyl cyclopentyl ether, tert.-butyl methyl ether, tert.-butyl ethyl ether, tert.-amyl methyl ether or mixtures thereof.

The reaction is carried out at low temperature, preferred in a range of −20° C. to 20° C., more preferably between −10° C. and 10° C.

The solvents are removed. It is preferred that this is done under reduced pressure. The product is then purified using commonly known methods. Compounds of formula (II) are not known from prior art.

Therefore a further embodiment of the present invention relates to compounds of formula (II)

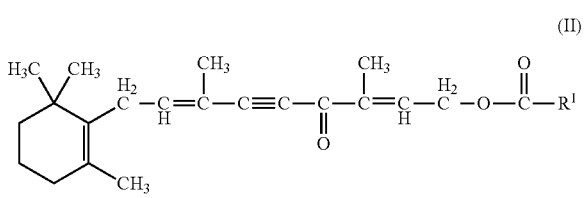

(II)

wherein $R^1$ signifies a $C_1$-$C_{15}$ alkyl moiety or a $C_2$-$C_{18}$ alkenyl moiety.

When $R^1$ is a $C_1$-$C_{15}$ alkyl moiety, then preferably the alkyl moiety is linear. Especially preferred alkyl moieties are methyl, ethyl and pentadecyl.

When $R^1$ is a $C_2$-$C_{18}$ alkenyl moiety, compound of formula (II) can have more than three C—C double bonds. Preferably the alkenyl moiety is unbranched.

Compounds of formula (II) can be in any stereoisomeric form. The compounds of formula (I) can be in an all-E-form or in an all-Z-form, as well as in any other E/Z-form.

It is possible that the compound of formula (II) is in an isomerically pure form, but it is also possible that compound of formula (II) is a mixture of at least two isomeric forms. These most preferred compounds of formula (II) are those wherein $R^1$ is methyl, ethyl or pentadecyl.

A compound of formula (II) is produced by the reaction of a compound of formula (III)

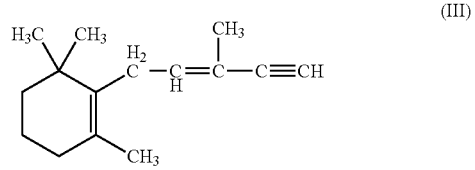

(III)

with a compound of formula (IV)

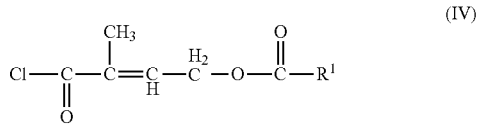

(IV)

Usually the reaction of compounds of formula (III) and of formula (IV) is carried out in polar aprotic solvents. Preferred solvents are ethers, e.g. THF, methyl-THF, methyl cyclopentyl ether, tert.-butyl methyl ether, tert.-butyl ethyl ether, tert.-amyl methyl ether or mixtures thereof.

The reaction of compounds of formula (III) and of formula (IV) is carried out in a preferred range of −20° C. to 60° C., more preferably between 15° C. and 40° C.

The reaction of compounds of formula (III) and of formula (IV) is preferably performed in presence of catalytic amounts of a palladium catalyst and a copper catalyst. The molar ratio of copper to palladium catalyst is in the range of 1.1:1 to 10:1, preferred 1.5:1 to 5:1, especially preferred 1.8:1 to 3:1. The ratio of substrate to palladium catalyst is in the range of 2000:1 to 10:1, preferably 1000:1 to 50:1.

The palladium catalyst can be chosen from the group of bis(triarylphosphine)palladium(II) dihalides and chelating bis(diarylphosphinoalkane) palladium(II) dihalides, wherein the alkane is a linear $C_2$ to $C_6$ alkyl moiety. The copper catalyst can be a copper(I) salt, preferably a copper(I) halide, more preferably copper(I) iodide.

Compounds of formula (III) can be produced according to the method known from the prior art. GB1034189 discloses a method for producing compounds of formula (III) which is therefore incorporated by reference.

Compounds of formula (IV) are not known from the prior art. The compounds of formula (IV) can be produced by chlorination of compounds of formula (V)

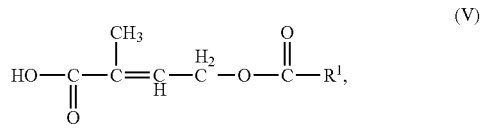

(V)

wherein $R^1$ signifies a $C_1$-$C_{15}$ alkyl moiety or a $C_2$-$C_{18}$ alkenyl moiety using at least one chlorination reactant.

When R is a $C_1$-$C_{15}$ alkyl moiety, then preferably the alkyl moiety is linear. Especially preferred alkyl moieties are methyl, ethyl and pentadecyl.

When $R^1$ is a $C_2$-$C_{18}$ alkenyl moiety, compound of formula (V) can have more than three C—C double bonds. Preferably the alkenyl moiety is unbranched.

Chlorination reactants are widely known and used. For the chlorination of compounds of formula (V) any chlorinating agents (or mixtures thereof) can be used.

Examples of chlorinating agents are oxalylchloride, phosphorus pentachloride, thionylchloride, phosphorus oxychloride, chlorine, chloric acid, antimony(V) chloride, hypochlorous acid, N-chlorosuccinimide, phosphorus trichloride, sulfurylchloride, carbon tetrachloride, cyanuric chloride.

Preferred chlorinating agents are oxalylchloride, phosphorus pentachloride, thionylchloride and phosphorus oxychloride.

The chlorinating agents are usually added in a slight molar excess in regard to the amount of compound of formula (V).

The reaction is usually carried out in a polar or non-polar solvents like toluene, N,N-dimethylformamide (DMF), dichloromethane, dichloroethane, 1-methyl-2-pyrrolidone (NMP), xylenes, or ethers.

The chlorination of the compounds of formula (V) is usually carried out at a temperature of from −20° C. to 100° C., preferably 0° C. to 50° C.

The compounds of formula (I) according to the present invention can be used in organic synthesis.

Preferably the new compounds are useful as intermediates (building blocks) in the synthesis of vitamin A or β-carotene or derivatives thereof, preferably vitamin A. Therefore a further embodiment of the present invention relates to the use of compounds of formula (I) in organic synthesis. A preferred embodiment of the present invention relates to the use of compounds of formula (I) as intermediates (building blocks) in the synthesis of vitamin A or β-carotene, preferably vitamin A.

EXAMPLES

Example 1

Reduction of 3,7-dimethyl-4-oxo-9-(2,6,6-trimethylcyclohex-1-enyl)nona-2,7-dien-5-ynyl acetate (IIa) to 4-hydroxy-3,7-dimethyl-9-(2,6,6-trimethylcyclohex-1-enyl)nona-2,7-dien-5-ynyl acetate (Ia)

In a 500 ml four-necked flask 1.95 g (5 mmol) of ketone of formula (IIa)

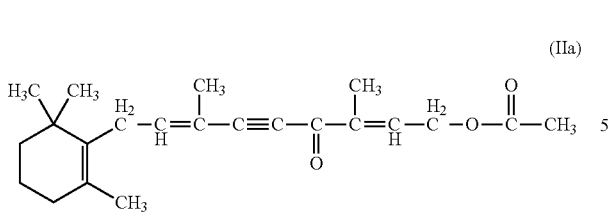

(IIa)

were dissolved in 300 ml of anhydrous THF. The yellow solution was cooled to 0° C. with an ice bath. Successively 10 ml (10 mmol) of (S)-2-methyl-CBS-oxazaborolidine (1M in toluene) and 1.2 ml (11.25 mmol) of borane dimethyl sulfide complex were added drop wise via syringe. After 40 minutes the colourless solution was warmed to 24° C. Then, 150 ml of methanol were added and stirring was continued until gas formation had ceased. The solvents were removed at 40° C. under reduced pressure (350 to 20 mbar). The crude product was obtained as yellow oil in a yield of 92%. The product (compound of formula (Ia)) was then purified. The yield of the purified product was 87%.

Example 2

4-chloro-3-methyl-4-oxobut-2-enyl acetate (Compound of formula (IVa))

3.2 g (19.73 mmol) of 2-methyl-4-acetyloxy-2-butenoic acid (compound of formula (Va)

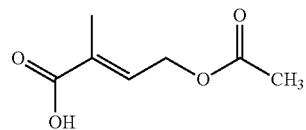

(Va)

were mixed with 11.4 ml of toluene and 300 μl of N,N-dimethylformamide (DMF). 2.78 g (21.70 mmol) of oxalyl-chloride were slowly added to the reaction mixture while keeping the temperature of the reaction mixture with a water bath at 20° C. After 2.5 hours of stirring at room temperature, the solvent was removed at 50° C. and 30 mbar. A red-brownish oil (3.83 g) was obtained which was purified. A slightly yellow liquid was obtained. The yield of 4-chloro-3-methyl-4-oxobut-2-enyl acetate (compound of formula (IVa)) was 99%.

Example 3

3,7-dimethyl-4-oxo-9-(2,6,6-trimethylcyclohex-1-enyl)nona-2,7-dien-5-ynyl acetate (Compound of Formula (IIa))

Under inert gas atmosphere 59.9 mg (0.308 mmol) of copper(I) iodide and 110.3 mg (0.154 mmol) of bis(triphenylphosphine)palladium(II) dichloride [(PPh$_3$)$_2$PdCl$_2$] were added to a 100 ml four-necked flask. At 23° C., 42.0 ml of anhydrous THF were added and the yellow suspension was stirred for 5 min. When 2.15 ml (15.4 mmol) of triethylamine were introduced drop wise via syringe an orange solution was obtained. Within 1 minute 3.10 g (15.4 mmol) of 4-chloro-3-methyl-4-oxobut-2-enyl acetate (compound of formula (IVa)) were added and the solution turned dark orange. Upon drop wise addition of 2.92 g (14.0 mmol) of 1,3,3-trimethyl-2-(3-methylpent-2-en-4-ynyl)cyclohex-1-ene (compound of formula (III))

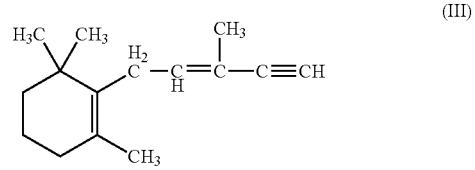

(III)

over 5 minutes a yellow suspension was formed. The reaction mixture was cooled to room temperature and monitored by GC and TLC. After 2 hours and 20 min at 23° C., all starting material was consumed. The reaction mixture was transferred into a separatory funnel, diluted with 80 ml of diethyl ether and washed with semi-concentrated sodium bicarbonate solution (80 ml). The layers were separated and the aqueous layer was extracted with diethyl ether (2×75 ml). The combined organic layers were washed with 80 ml of semi-sat. sodium bicarbonate solution, dried over sodium sulphate and concentrated to dryness. The crude product (compound of formula (IIa)

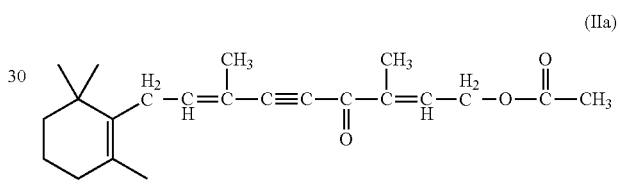

(IIa)

was obtained as brown oil (5.44 g, 82% purity, 93% yield) and purified by column chromatography and charcoal treatment.

The invention claimed is:

1. A compound of formula (I):

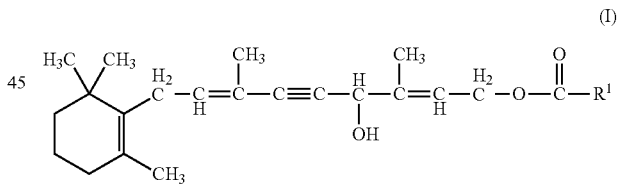

(I)

wherein R$^1$ signifies a C$_1$-C$_{15}$ alkyl moiety or a C$_2$-C$_{18}$ is alkenyl moiety.

2. The compound according to claim 1, wherein R$^1$ is a linear C$_1$-C$_{15}$ alkyl moiety.

3. The compound according to claim 1, wherein R$^1$ is methyl, ethyl or pentadecyl.

4. The compound according to claim 1, wherein R$^1$ is an unbranched C$_2$-C$_{18}$ alkenyl moiety having more than three C-C double bonds.

5. The compound according to claim 1, wherein the compound of formula (I) is a pure stereoisomeric form.

6. The compound according to claim 1, wherein the compound of formula (I) is a mixture of stereoisomeric forms.

7. A process for production of a compound of formula (I) according to claim 1, wherein the process comprises reducing, in the presence of 2-methyl-CBS-oxazaborolidine and borane dimethyl sulphide, a compound of formula (II):

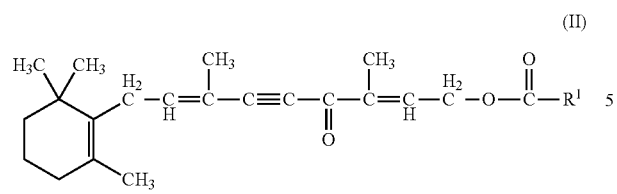
(II)
wherein R¹ signifies a $C_1$-$C_{15}$ alkyl moiety or a $C_2$-$C_{18}$ alkenyl moiety.
* * * * *